(12) United States Patent
Wallin

(10) Patent No.: US 6,220,242 B1
(45) Date of Patent: Apr. 24, 2001

(54) DOSING DEVICE SUITABLE FOR REGULATING A VAPOR CONCENTRATION IN AN ANESTHESIA/VENTILATOR APPARATUS

(75) Inventor: Sten Wallin, Hägersten (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/261,185

(22) Filed: Mar. 3, 1999

(30) Foreign Application Priority Data

Mar. 27, 1998 (SE) .................................................. 9801074

(51) Int. Cl.$^7$ ..................... A61M 16/00; A61M 16/01; A61M 16/18
(52) U.S. Cl. ................... 128/203.12; 128/204.22; 128/204.21; 128/205.24; 261/26; 261/28
(58) Field of Search ..................... 128/203.12, 204.22, 128/204.21, 205.24; 261/26, 28

(56) References Cited

U.S. PATENT DOCUMENTS

| 4,038,980 | 8/1977 | Fodor . | |
|---|---|---|---|
| 5,235,971 | * 8/1993 | Falb et al. | 128/203.14 |
| 5,237,990 | * 8/1993 | Psaros et al. | 128/204.21 |
| 5,243,973 | * 9/1993 | Falb et al. | 128/203.27 |
| 5,509,406 | * 4/1996 | Kock et al. | 128/203.14 |
| 5,771,882 | * 6/1998 | Psaros et al. | 128/203.12 |

FOREIGN PATENT DOCUMENTS

| 0 545 567 | 6/1993 | (EP) . |
| WO 92/19303 | 11/1992 | (WO) . |

* cited by examiner

*Primary Examiner*—Dennis Ruhl
*Assistant Examiner*—Mital Patel
(74) *Attorney, Agent, or Firm*—Schiff Hardin & Waite

(57) ABSTRACT

A dosing device for regulating the concentration of a liquid vapor, produced by vaporizing liquid from a liquid source, in a carrier gas has on-off valve which is automatically operable by a valve controller and which is connectable to one or both of the liquid and the carrier gas. A flow meter is provided in the flow path of the liquid and generates an output signal proportional to the flow of the liquid supplied for vaporization. This signal is supplied to the controller which cooperates with the valve to automatically regulate the supply of one or both of the liquid or carrier gas dependent on the output signal.

7 Claims, 2 Drawing Sheets

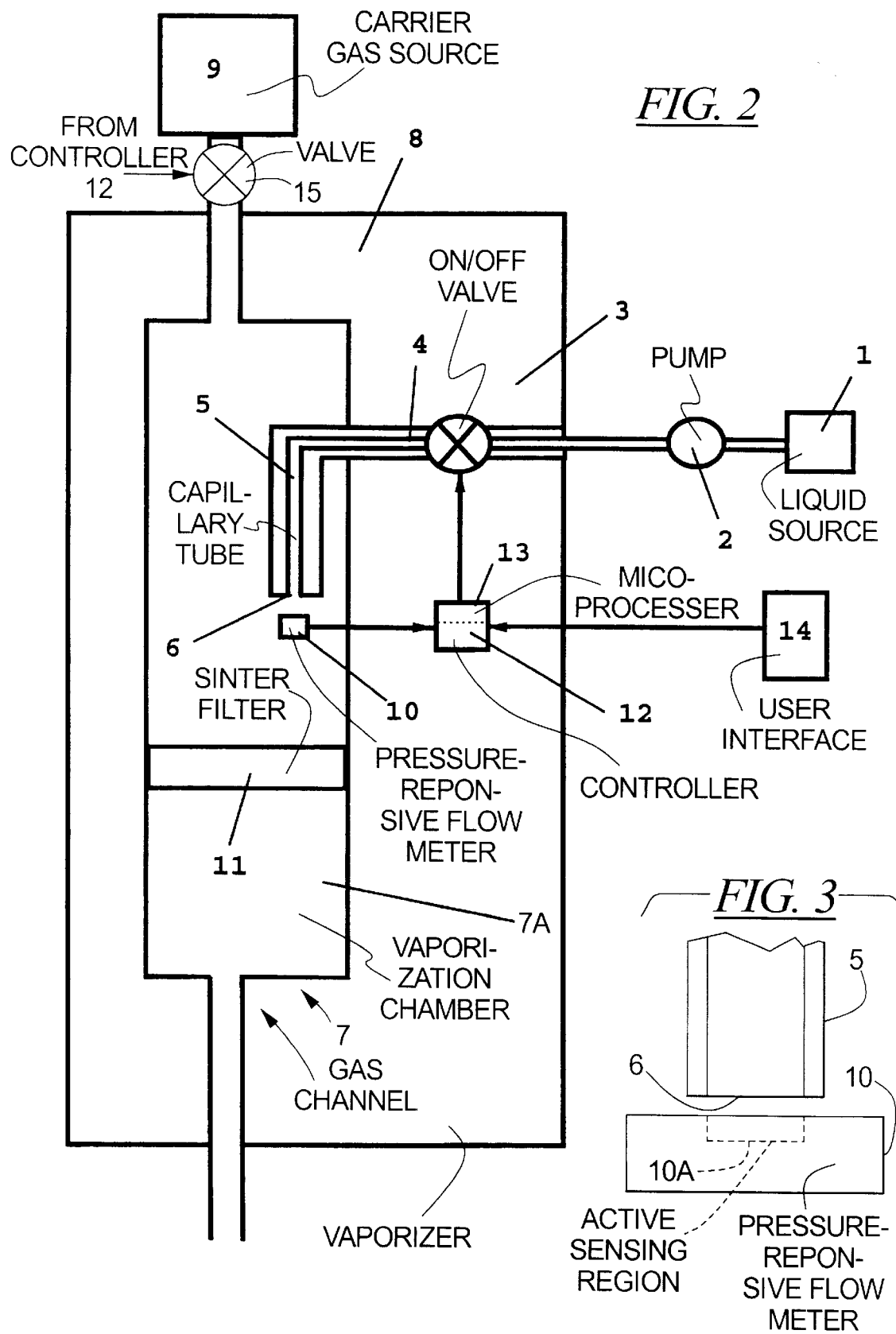

DOSING DEVICE SUITABLE FOR REGULATING A VAPOR CONCENTRATION IN AN ANESTHESIA/VENTILATOR APPARATUS

BACKGROUND OF THE INVENTION

1. Field of the Invention

The present invention relates to a dosing device and in particular to a dosing device suitable for use in an anaesthesia machine or ventilator to regulate the concentration of a liquid vapor, such as an anaesthetic vapor, in a carrier gas component of a breathing gas.

2. Description of the Prior Art

It is common to administer liquid anaesthetic agents to a patient as a gas. This is done by vaporizing the liquid and then conducting the vaporized anaesthetic to the patient in a carrier gas. It is important that the amount of anaesthetic agent is accurately controlled and this is generally achieved in one of two ways; either by controlling the flow rate of the carrier gas through a reservoir of liquid anaesthetic or by controlling the dose of liquid anaesthetic to be supplied for vaporization. If a fault occurs in a device operating in the first way then relatively high doses can be taken from the reservoir. Even if other security measures for the patient are provided and are triggered, the patient may still be exposed to a quantity that could cause discomfort, and in the worst case even a harmful or lethal quantity.

A known dosing device for controlling the dose of liquid anaesthetic to be supplied for vaporization is described in WO 92/19303 (BOC Group PLC) and has a variable volume pump which can be operated to define the dose to be supplied by varying the volume in a controlled manner using a stepper motor. This device, however, requires that the pump and stepper motor are manufactured to a high mechanical tolerance, which adds to the cost of such a device as well as to the manufacturing difficulties. Additionally the generation of an intermittent flow, particularly of low flow rate, may be problematic since this requires accurate control of the pump volume over the majority of its stroke length.

SUMMARY OF THE INVENTION

An object of the present invention is to provide a dosing device in which the need for metering variations of pump volume is avoided.

This is achieved by a dosing device according to the invention wherein the flow of the liquid to be vaporized is monitored directly using a flow meter, the output of which operates a flow control component, for example a variable flow restriction, to regulate the supply of one or both of the liquid and carrier gas. Thus the need to determine and control exact pump chamber volume changes is removed and the dose may be supplied using a less sophisticated and relatively inexpensive over-pressure and on off valve arrangement.

Moreover, as flow control may be more readily achieved than volume control and as the supply is directly controlled from the actual liquid flow a controllable intermittent dose can be more readily achieved.

Preferably the flow meter has a pressure sensor adapted to provide a measure of the flow from the pressure exerted by incident liquid. Such a sensor is much better suited to the measurement of the relatively small flows that may be present in the dosing device than, for example, resistance type flow meters. Moreover, such a pressure sensor may be readily constructed, using current technology, to present little obstruction to the overall fluid flow path.

The dosing device can have a guide component, such as a capillary tube, for directing substantially all of the flowing liquid to the flow meter. This has the advantage, particularly at low doses, that the signal from the flow meter is a direct measure of the total amount of flowing liquid. Moreover, the capillary tube, because of its dimensions, may provide a substantially laminar liquid flow to the sensor. Thus a more accurate flow measurement may be made since the flow characteristics are more predictable.

DESCRIPTION OF THE DRAWINGS

FIG. 2 is a schematic block diagram of a second embodiment of a dosing device according to the present invention.

FIG. 3 is an enlarged view of a portion of the dosing device in each of FIGS. 1 and 2.

DESCRIPTION OF THE PREFERRED EMBODIMENTS

Figure 1:
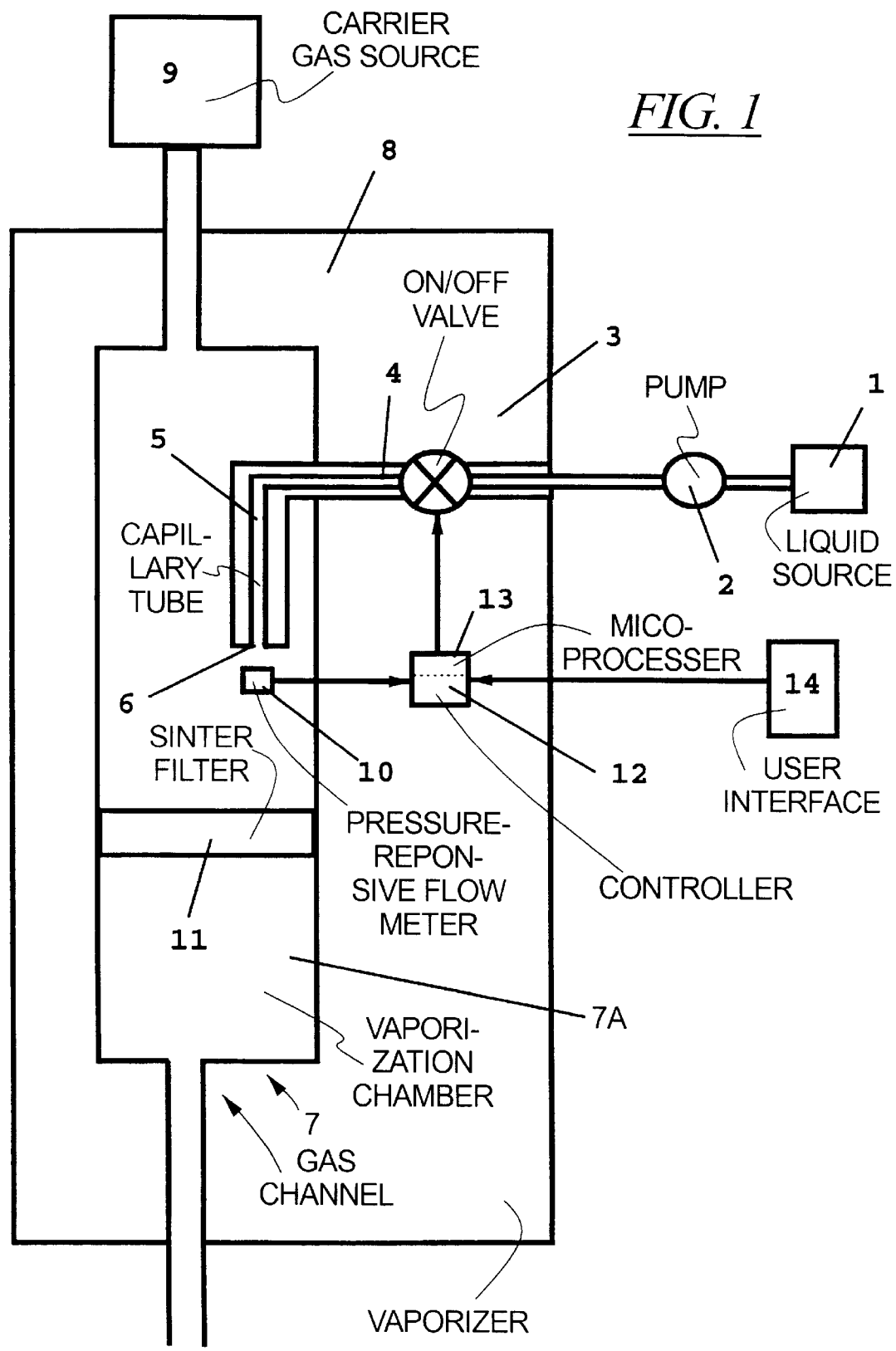
FIG. 1 is a schematic block diagram of a first embodiment of a dosing device according to the present invention.

In the inventive dosing device shown in FIG. 1, liquid anaesthetic from a liquid source 1 is pumped, using a pump 2, via an automatically controllable on-off valve 3 into an inlet 4 of a capillary tube 5. The tube 5 has an outlet 6 into a gas channel 7 of a vaporizer 8. A cylinder 9 of gas is also connected to the gas channel 7 and flows past the outlet of the capillary tube 5 to carry the liquid anaesthetic which is then vaporized in this so called "carrier gas" before inspiration by a patient. Vaporization takes place, by any suitable means known to those of ordinary skill in the art, and a vaporization chamber 7A, which is schematically indicated as an enlarged portion of the gas channel 7.

A pressure sensor-type (i.e., pressure responsive) flow meter 10 is also placed within the gas channel 7 downstream of the outlet 6 of the capillary tube 5 so that the capillary tube 5 functions as a guide element causing substantially all of the liquid flowing from the capillary 5 to be incident upon and registered by the pressure sensor of the flow meter 10 before vaporization. Additionally, the vaporizer may contain a sinter filter 11, downstream of the flow meter 10, which is well known in the art and has a large number of capillary through-paths (for example created by the close packing of spheres which may constitute the filter 11) that produce forces on the liquid to enhance its vaporization.

A control arrangement formed by the valve 3 and a valve controller 12 is operably connected to the flow meter 10, which emits a signal to the controller 12 representative of the flow rate of the liquid anaesthetic measured by the meter 10. The controller 12 includes a suitably programmed microprocessor 13 and a timer, which here is a digital timer implemented in the microprocessor 13, which acts to measure the time elapsed since the valve 3 was opened. The controller 12 is adapted to calculate from the input flow rate and from the elapsed time the quantity of liquid delivered into the gas channel 7. The controller 12 further provides control signals to open and close the valve 3, thereby regulating the eventual concentration of anaesthetic vapor in the carrier gas, and operates to close the valve 3 when a predetermined dose (which is either entered as a fixed value into a memory store of the microprocessor when the device is manufactured or entered as a variable value from a user interface 14, such as a conventional keypad) has been delivered.

Preferably the meter 10 and the capillary tube 5 are arranged to minimize "dead space" between the valve 3 and the meter 10 from which space liquid will continue to be supplied after the valve 3 is closed and which therefore represents a minimum dose. As shown in FIG. 3, the pressure responsive flow meter 10 has an active sensing region 10A, and the guide element formed by the capillary tube 5 has a cross-sectional area so that substantially all of the liquid in the flow path from the liquid source 1 is incident on the active region 10A.

As shown in FIG. 2, a valve 15, controlled by the controller 12 dependent on the output of the flow meter 10, is located near the outlet of the carrier gas supply 9. Another alternative is to regulate the liquid flow by controlling the operation of the pump 2 used to supply liquid to be vaporized in dependence of the measured liquid flow.

Although modifications and changes may be suggested by those skilled in the art, it is the intention of the inventor to embody within the patent warranted hereon all changes and modifications as reasonably and properly come within the scope of his contribution to the art.

I claim as my invention:

1. In a vaporizer for use with a liquid source and a carrier gas source, said vaporizer having a first inlet adapted for connection to said liquid source and a second inlet adapted for connection to said carrier gas source, and a vaporizing chamber wherein liquid from said liquid source is vaporized, as vaporized liquid, in carrier gas from said carrier gas source, the improvement, comprising:

flow path defining structure for creating a flow path communicating with said first inlet and an interior of said vaporizing chamber, said flow path being adapted to contain liquid received from said liquid source;

an adjustable liquid flow valve disposed in said flow path;

a flow meter disposed in said flow path which generates an output signal proportional to a flow of said liquid in said flow path before vaporization of said liquid; and a controller operably connected to said flow meter and receiving said output signal therefrom and operably connected to said valve for operating said valve to regulate a supply of said liquid in said flow path from said first inlet to said interior of said vaporizing chamber dependent on said signal from said flow meter.

2. The vaporizer thereof of claim 1 wherein said adjustable valve has a variable flow restriction operable by said control unit to vary said supply of liquid.

3. The vaporizer of claim 1 wherein said flow meter has an active region for detecting flow of said liquid, and wherein said flow path defining structure comprises a guide element connected in said flow path adapted for directing liquid flowing in said flow path onto said active region of said flow meter, said guide element having a cross-sectional area having a size so that substantially all of said liquid in said flow path is incident on said active region.

4. The vaporizer of claim 3 wherein said guide element is therefor a capillary tube connected between said first inlet and said interior of said vaporizing chamber, and wherein said adjustable valve is disposed to adjust flow of said liquid through said capillary tube, controlled by said controller.

5. The vaporizer of claim 4 wherein said capillary tube has a capillary tube outlet, and wherein said active region of said flow meter is disposed proximate said capillary tube output.

6. The vaporizer of claim 1 wherein said flow meter comprises a pressure-responsive flow meter.

7. The vaporizer of claim 1 wherein said adjustable valve is a first adjustable valve, and said improvement comprising a furtherflow path defining structure for creating a further flow path communicating with said second inlet and said interior of said vaporizing chamber, said further flow path being adapted to contain carrier gas received from said carrier gas source, and an adjustable gas flow valve disposed in said further flow path, said adjustable gas flow valve being operably connected to said controller and being controlled by said controller to adjust a flow of carrier gas in said further flow path dependent on said output signal from said flow meter.

* * * * *